US008615290B2

(12) United States Patent
Lin et al.

(10) Patent No.: US 8,615,290 B2
(45) Date of Patent: Dec. 24, 2013

(54) SEAMLESSLY EMBEDDED HEART RATE MONITOR

(75) Inventors: Gloria Lin, San Ramon, CA (US);
Taido Nakajima, Cupertino, CA (US);
Pareet Rahul, Markham (CA); Andrew Hodge, Palo Alto, CA (US)

(73) Assignee: Apple Inc., Cupertino, CA (US)

( * ) Notice: Subject to any disclaimer, the term of this patent is extended or adjusted under 35 U.S.C. 154(b) by 847 days.

(21) Appl. No.: 12/358,905

(22) Filed: Jan. 23, 2009

(65) Prior Publication Data

US 2010/0113950 A1    May 6, 2010

Related U.S. Application Data

(60) Provisional application No. 61/111,498, filed on Nov. 5, 2008.

(51) Int. Cl.
*A61B 5/0402*    (2006.01)

(52) U.S. Cl.
USPC .............................. 600/509; 607/36; 340/5.82

(58) Field of Classification Search
USPC .............................. 600/509; 607/36; 340/5.82
See application file for complete search history.

(56) References Cited

U.S. PATENT DOCUMENTS

| | | | |
|---|---|---|---|
| 4,635,646 A * | 1/1987 | Gilles et al. | 600/509 |
| 6,522,915 B1 * | 2/2003 | Ceballos et al. | 600/509 |
| 7,689,833 B2 | 3/2010 | Lange | |
| 2006/0026521 A1 | 2/2006 | Hotelling et al. | |
| 2006/0026535 A1 | 2/2006 | Hotelling et al. | |
| 2008/0076972 A1 | 3/2008 | Dorogusker et al. | |
| 2008/0113650 A1 | 5/2008 | Engstrom | |
| 2009/0070266 A1 | 3/2009 | Shah et al. | |
| 2010/0011388 A1 | 1/2010 | Bull et al. | |

FOREIGN PATENT DOCUMENTS

| | | |
|---|---|---|
| JP | 2008073461 A | 4/2008 |
| JP | 2008073462 A | 4/2008 |

* cited by examiner

*Primary Examiner* — Carl H Layno
*Assistant Examiner* — Alyssa M Alter
(74) *Attorney, Agent, or Firm* — Van Court & Aldridge LLP

(57) ABSTRACT

This is directed to an electronic device having an integrated sensor for detecting a user's cardiac activity and cardiac electrical signals. The electronic device can include a heart sensor having several leads for detecting a user's cardiac signals. The leads can be coupled to interior surfaces of the electronic device housing to hide the sensor from view, such that electrical signals generated by the user can be transmitted from the user's skin through the electronic device housing to the leads. In some embodiments, the leads can be coupled to pads placed on the exterior of the housing. The pads and housing can be finished to ensure that the pads are not visibly or haptically distinguishable on the device, thus improving the aesthetic qualities of the device. Using the detected signals, the electronic device can identify or authenticate the user and perform an operation based on the identity of the user. In some embodiments, the electronic device can determine the user's mood from the cardiac signals and provide data related to the user's mood.

20 Claims, 6 Drawing Sheets

SEAMLESSLY EMBEDDED HEART RATE MONITOR

CROSS-REFERENCE TO RELATED APPLICATION

This application claims priority to U.S. Provisional Application No. 61/111,498, filed Nov. 5, 2008, which is incorporated by reference herein in its entirety.

BACKGROUND OF THE INVENTION

This is directed to providing a seamless heart-rate monitor in an electronic device.

Many electronic devices are used to store personal or confidential information. In particular, portable electronic devices such as cellular telephones, personal assistants, and music players are often used to store or access e-mail, contact lists, communications history, remotely accessed accounts (e.g., telephone, banking or credit card accounts), or other information that a user may regard as personal or private. In addition, several users may use the same electronic device. For example, several users in a household may use the same computer or portable music player. As another example, a user may lend an electronic device to a friend (e.g., lend an iPod, available from Apple Inc. to a friend for a workout or a trip). To enhance each user's experience with the electronic device, the electronic device can include several profiles that can be loaded and provided to the users of the device. Each profile can be associated with a particular user, and include several settings that allow the electronic device interface user interaction components, and available data or applications to be personalized for the user.

The electronic device can use several approaches to identify the user of the electronic device and provide access to the user's private and personal information, or to load the user's personal profile. In some embodiments, the electronic device can identify or authenticate a user based on an input provided by the user, such as a password or key provided using an input mechanism. In some embodiments, the electronic device can include one or more sensors operative to detect a fingerprint, voice print, facial features, or other biometric characteristics of a user.

Other biometric-based approaches can be used to authenticate a user. In some embodiments, an electronic device can authenticate a user based on the attributes of the user's heartbeat. For example, the durations of particular portions of a user's heart rhythm, or the relative size of peaks of a user's electrocardiogram (EKG) can be processed and compared to a stored profile to authenticate a user of the device. To detect a user's heartbeat or heart rhythm, however, the electronic device must provide at least two leads that the user contacts to detect the user's cardiac signals. Although the leads can simply be placed on the exterior surface of the device housing, for example in a defined location where the user may place a finger, this approach is not aesthetically pleasing, and may cause some prospective buyers to consider other devices. In addition, such an approach may require the user to perform a specific authentication action—viz., placing a finger on the one or more leads, then unlocking or accessing the electronic device features (e.g., by moving a slider across the screen). This additional step may in fact be so encumbering that users disable the authentication feature and instead use an unsecured electronic device.

SUMMARY OF THE INVENTION

This is directed to an electronic device having a seamlessly integrated cardiac sensor. The cardiac sensor can be integrated in any suitable portion of the electronic device, including for example a portion with which the user is typically in contact (e.g., an input mechanism or a housing held by the user), or metallic or conductive portions of the device.

The electronic device can include any suitable type of electronic device, including for example a portable electronic device that the user may hold in hand (e.g., a portable media player or a cellular telephone), a larger portable electronic device (e.g., a laptop computer), or a substantially fixed electronic device. The electronic device may include software or hardware operative to process the output of a cardiac sensor to extract, from the received output, characteristics of the user's heartbeat, heart rate, or other cardiac signals. For example, the electronic device may extract one or more characteristic durations associated with the user's heart rate. As another example, the electronic device may extract one or more characteristic amplitudes or amplitude ratios associated with the user's heart rate.

Once the electronic device has identified one or more characteristics of the user's heart rate, heartbeat, or other cardiac signals, the electronic device can compare the one or more identified characteristics with cardiac signal characteristics of authorized users that have been stored in memory. In response to determining that the identified characteristics correspond to those of an authorized user (e.g., match those stored in memory), the electronic device can provide the user with access to the electronic device and load the identified user's personal settings and data.

To determine the user's heart rate, heartbeat, or other cardiac signals, the electronic device can include one or more sensors embedded in the device. The one or more sensors can include leads for receiving electrical signals from the user's heart. For example, the one or more sensors can include leads associated with the user's left and right sides, and lead associated with the ground. To provide an electrical signal from the user to the processing circuitry, the leads can be exposed such that the user may directly contact the leads, or may instead or in addition be coupled to an electrically conductive portion of the device enclosure (e.g., a metallic bezel or housing forming the exterior of the device).

Because each electronic device can include several leads, the leads may be electrically isolated to avoid shorting or interference among leads. In some embodiments, an electrically isolating component can be inserted between adjacent leads. Alternatively, if the electronic device enclosure is constructed from a material having insufficient conductivity for transmitting detected cardiac electrical signals, the distance along the enclosure between adjacent leads can be sufficient to isolate the leads. In addition, to ensure that the aesthetic appeal and appearance of the electronic device is retained, one or more of the isolating components, the leads themselves, and the device enclosure can be finished using a suitable process to disguise the leads.

In some embodiments, if the electrical conductivity of portions of the electronic device enclosure and the leads are suitably selected and designed, the leads can be positioned underneath the exterior surface of the enclosure while providing sufficient conductivity for detecting cardiac electrical signals and avoiding shorting or interference between adjacent leads. For example, the sensor leads can be constructed from a silver based compound having high electrical conductivity, while the electronic device enclosure can be constructed from steel and aluminum, both having lower electrical conductivity. By placing several leads at substantially larger distances apart along the electronic device enclosure than the thickness of the enclosure, electronic signals can be transmitted through the steel or aluminum enclosure to a silver based lead underneath the enclosure, but not along the surface of the enclosure to cause adjacent leads to short.

BRIEF DESCRIPTION OF THE DRAWINGS

The above and other features of the present invention, its nature and various advantages will be more apparent upon consideration of the following detailed description, taken in conjunction with the accompanying drawings in which.

DETAILED DESCRIPTION

Figure 1:
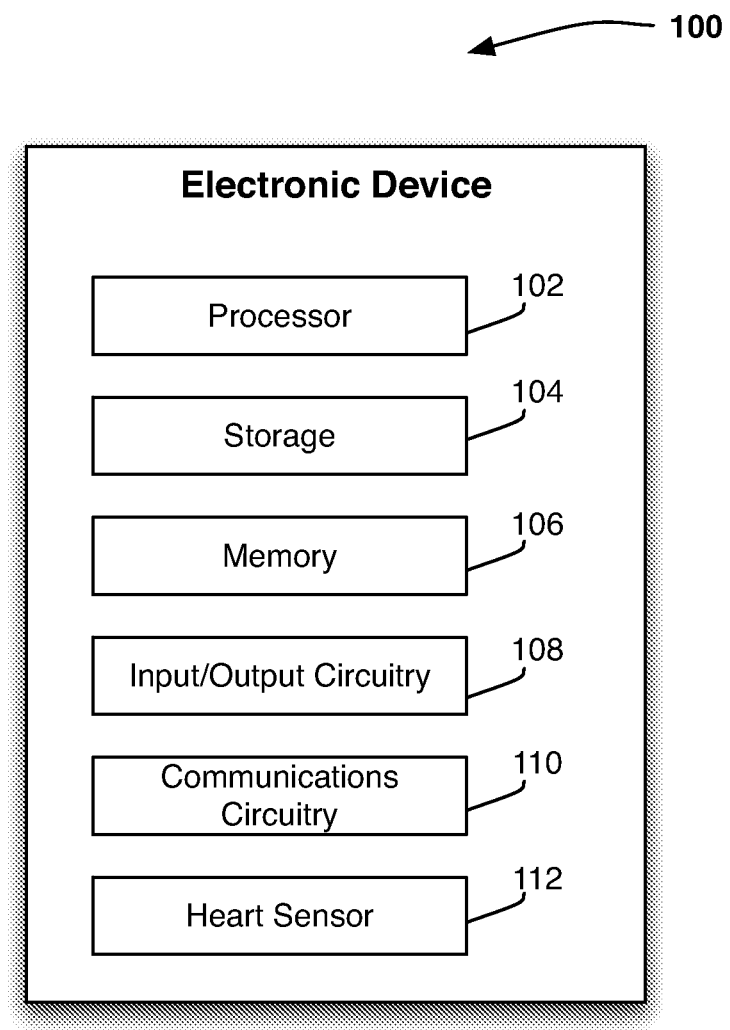
FIG. 1 is a schematic view of an illustrative electronic device for receiving the output of one or more sensors in accordance with one embodiment of the invention.

FIG. 1 is a schematic view of an illustrative electronic device for receiving the output of one or more sensors in accordance with one embodiment of the invention. Electronic device 100 can include control circuitry 102, storage 104, memory 106, input/output circuitry 108, communications circuitry 110, and heart sensor 112. In some embodiments, one or more of electronic device components 100 can be combined or omitted (e.g., combine storage 104 and memory 106). In some embodiments, electronic device 100 can include other components not combined or included in those shown in FIG. 1 (e.g., motion detection components, a power supply such as a battery or kinetics, a display, bus, or input mechanism), or several instances of the components shown in FIG. 1. For the sake of simplicity, only one of each of the components is shown in FIG. 1.

Control circuitry 102 can include any processing circuitry or processor operative to control the operations and performance of electronic device 100. For example, control circuitry 100 can be used to run operating system applications, firmware applications, media playback applications, media editing applications, or any other application. In some embodiments, the control circuitry can drive a display and process inputs received from a user interface.

Storage 104 can include, for example, one or more storage mediums including a hard-drive, solid state drive, flash memory, permanent memory such as ROM, any other suitable type of storage component, or any combination thereof. Storage 104 can store, for example, media data (e.g., music and video files), application data (e.g., for implementing functions on device 100), firmware, user preference information data (e.g., media playback preferences), authentication information (e.g. libraries of data associated with authorized users), lifestyle information data (e.g., food preferences), exercise information data (e.g., information obtained by exercise monitoring equipment), transaction information data (e.g., information such as credit card information), wireless connection information data (e.g., information that can enable electronic device 100 to establish a wireless connection), subscription information data (e.g., information that keeps track of podcasts or television shows or other media a user subscribes to), contact information data (e.g., telephone numbers and email addresses), calendar information data, and any other suitable data or any combination thereof.

Memory 106 can include cache memory, semi-permanent memory such as RAM, and/or one or more different types of memory used for temporarily storing data. In some embodiments, memory 106 can also be used for storing data used to operate electronic device applications, or any other type of data that can be stored in storage 104. In some embodiments, memory 106 and storage 104 can be combined as a single storage medium.

Input/output circuitry 108 can be operative to convert (and encode/decode, if necessary) analog signals and other signals into digital data. In some embodiments, input/output circuitry 108 can also convert digital data into any other type of signal, and vice-versa. For example, input/output circuitry 108 can receive and convert physical contact inputs (e.g., from a multi-touch screen), physical movements (e.g., from a mouse or sensor), analog audio signals (e.g., from a microphone), or any other input. The digital data can be provided to and received from processor 102, storage 104, memory 106, heart sensor 112, or any other component of electronic device 100. Although input/output circuitry 108 is illustrated in FIG. 1 as a single component of electronic device 100, several instances of input/output circuitry can be included in electronic device 100.

Electronic device 100 can include any suitable mechanism or component for allowing a user to provide inputs to input/output circuitry 108. For example, electronic device 100 can include any suitable input mechanism, such as for example, a button, keypad, dial, a click wheel, or a touch screen. In some embodiments, electronic device 100 can include a capacitive sensing mechanism, or a multi-touch capacitive sensing mechanism. Some sensing mechanisms are described in commonly owned Hotelling et al. U.S. Patent Application Publication No. 2006/0026521, published Feb. 2, 2006, and entitled "Gestures for Touch Sensitive Input Device," and Hotelling et al. U.S. Patent Application Publication No. 2006/0026535, published Feb. 2, 2006, and entitled "Mode-Based Graphical User Interfaces for Touch Sensitive Input Devices," both of which are incorporated herein in their entirety.

In some embodiments, electronic device 100 can include specialized output circuitry associated with output devices such as, for example, one or more audio outputs. The audio output can include one or more speakers (e.g., mono or stereo speakers) built into electronic device 100, or an audio component that is remotely coupled to electronic device 100 (e.g., a headset, headphones or earbuds that can be coupled to communications device with a wire or wirelessly).

In some embodiments, I/O circuitry 108 can include display circuitry (e.g., a screen or projection system) for providing a display visible to the user. For example, the display circuitry can include a screen (e.g., an LCD screen) that is incorporated in electronics device 100. As another example, the display circuitry can include a movable display or a projecting system for providing a display of content on a surface remote from electronic device 100 (e.g., a video projector). In some embodiments, the display circuitry can include a coder/decoder (Codec) to convert digital media data into analog signals. For example, the display circuitry (or other appropriate circuitry within electronic device 100) can include video Codecs, audio Codecs, or any other suitable type of Codec.

The display circuitry also can include display driver circuitry, circuitry for driving display drivers, or both. The display circuitry can be operative to display content (e.g., media playback information, application screens for applications implemented on the electronic device, information regarding ongoing communications operations, information regarding incoming communications requests, or device operation screens) under the direction of control circuitry 102. Alternatively, the display circuitry can be operative to provide instructions to a remote display (e.g., display 130, FIG. 1).

Communications circuitry 110 can include any suitable communications circuitry operative to connect to a communications network and to transmit communications (e.g., voice or data) from communications device 100 to other devices within the communications network. Communications circuitry 110 can be operative to interface with the communications network using any suitable communications protocol such as, for example, Wi-Fi (e.g., a 802.11 protocol), Bluetooth®, radio frequency systems (e.g., 900 MHz, 1.4 GHz, and 5.6 GHz communication systems), infrared, GSM, GSM plus EDGE, CDMA, quadband, and other cellular protocols, VOIP, or any other suitable protocol.

In some embodiments, communications circuitry 110 can be operative to create a communications network using any suitable communications protocol. For example, communications circuitry 110 can create a short-range communications network using a short-range communications protocol to connect to other devices. For example, communications circuitry 110 can be operative to create a local communications network using the Bluetooth® protocol to couple electronic device 100 with a Bluetooth® headset.

Electronic device 100 can include one more instances of communications circuitry 110 for simultaneously performing several communications operations using different communications networks, although only one is shown in FIG. 1 to avoid overcomplicating the drawing. For example, electronic device 100 can include a first instance of communications circuitry 110 for communicating over a cellular network, and a second instance of communications circuitry 110 for communicating over Wi-Fi or using Bluetooth®. In some embodiments, the same instance of communications circuitry 110 can be operative to provide for communications over several communications networks.

In some embodiments, electronic device 100 can be coupled a host device for data transfers, synching the communications device, software or firmware updates, providing performance information to a remote source (e.g., providing riding characteristics to a remove server) or performing any other suitable operation that can require electronic device 100 to be coupled to a host device. Several electronic devices 100 can be coupled to a single host device using the host device as a server, and instead or in addition electronic device 100 can be coupled to several host devices (e.g., for each of the plurality of the host devices to serve as a backup for data stored in electronic device 100).

Heart sensor 112 can include any suitable sensor operative to detect a user's heartbeat, heart rate, or any other signal generated by the user's heart. In some embodiments, heart sensor 112 can serve as an EKG monitor. Heart sensor 112 can include one or more leads connected to the exterior of the electronic device such that the user may contact one or more of the leads to provide an electrical signal associated with the user's heart to heart sensor 112. The cardiac signals detected by the heart sensor leads can be coupled to a processor incorporated in heart sensor 112, or instead provided to processor 102. The processor may then analyze the received signals and generate, from the received signals, one or more characteristic quantities of the user's heartbeat or heart rate for authentication.

The heart sensor leads can be constructed from any suitable material. In some embodiments, the heart sensor leads can be constructed from a specific material selected for particular conductive properties that permit a more effective transmission of the electrical signals reflecting the user's cardiac activity. For example, the heart sensor leads can be constructed from a silver based compound, which can provide superior conductivity relative to other metallic compounds (e.g., steel or aluminum). In addition, the size and location of the leads can be selected to ensure that sufficient contact is made between the user (e.g., the user's hand or finger) and the leads for cardiac signals to be detected. For example, each lead can include a pad or extended area placed on the outer or inner surface of an electronic device bezel or housing. The pad or extended area can then be coupled to a wire or other connector for providing cardiac signals to a processor for processing. As another example, an entire portion of the electronic device enclosure (e.g., a portion of a bezel or housing) can serve as a lead for the heart sensor. In such embodiments, the portion of the enclosure can be sufficiently electrically isolated from other conductive portions of the electronic device housing to ensure that lead portions of the device do not short. In some embodiments, an accessory coupled to the electronic device can be used to detect a user's heart rate. For example, the leads can be located in one or more earbuds or in a headset, for example as is described in commonly assigned U.S. Patent Application Publication No. 2008/0076972, published Mar. 27, 2008, entitled "Integrated Sensors For Tracking Performance Metrics," which is incorporated by reference herein in its entirety.

Figure 2:
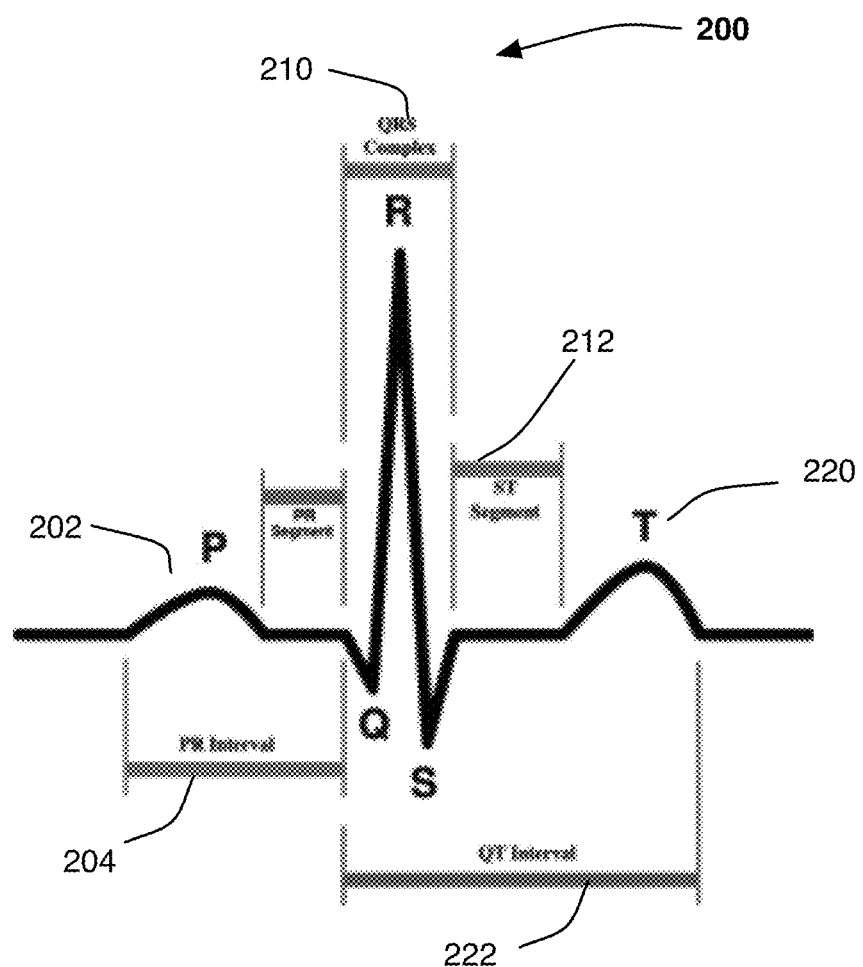
FIG. 2 is a graphical representation of illustrative electrical activity of a heart during a heartbeat.

Using a heart sensor, the electronic device can detect and analyze the electrical activity of the heart over time. FIG. 2 is a graphical representation of illustrative electrical activity of a heart during a heartbeat. Representation 200 may include a plot of the variation of the heart's electrical potential over time. A typical heartbeat may include several variations of electrical potential, which may be classified into waves and a complex. For example, representation 200 can include P wave 202, QRS complex 210, and T wave 220. Some representations can in addition include a U wave (not shown). The P wave can represent normal atrial depolarization, when the main electrical vector spreads from the right atrium to the left atrium. The shape and duration of the P wave can be related to the size of the user's atrium (e.g., indicating atrial enlargement), and can be a first source of heartbeat characteristics unique to a user.

The QRS complex can correspond to the depolarization of the heart ventricles, and can be separated into three distinct waves—a Q wave, a R wave and a S wave. Because the ventricles contain more muscle mass than the atria, the QRS complex is larger than the P wave. In addition, the His/Purkinje system of the heart, which can increase the conduction velocity to coordinate the depolarization of the ventricles, can cause the QRS complex to look "spiked" rather than rounded. The duration of the QRS complex of a healthy heart can be in the range of 60 to 100 ms, but can vary due to abnormalities of conduction. The duration of the QRS complex can therefore serve as a second source of heartbeat characteristics unique to a user.

The duration, amplitude, and morphology of each of the Q, R and S waves can vary in different individuals, and in particular can vary significantly for users having cardiac diseases or cardiac irregularities. For example, a Q wave that is greater than ⅓ of the height of the R wave, or greater than 40 ms in duration can be indicative of a myocardial infarction and provide a unique characteristic of the user's heart. Similarly, other healthy ratios of Q and R waves can be used to distinguish different users' heartbeats.

Representation 200 may include one or more characteristic durations or intervals that can be used to distinguish different users. For example, representation 200 can include PR interval 204 and ST segment 212. PR interval 204 can be measured from the beginning of P wave 202 to the beginning of QRS complex 210. PR interval 204 can typically last 120 to 200 ms. A PR interval 204 having a different duration can indicate one or more defects in the heart, such as a first degree heart block (e.g., PR interval 204 lasting more than 200 ms), a pre-excitation syndrome via an accessory pathway that leads to early activation of the ventricles (e.g., PR interval 204 lasts less than 120 ms), or another type of heart block (e.g., PR interval 204 is variable). ST segment 212 can be measured from QRS complex 210 to T wave 220, for example starting at the junction between QRS complex 210 and ST segment 212 and ending at the beginning of T wave 220. ST segment 212 can typically last from 80 to 120 ms, and normally has a slight upward concavity. The combination of the length of ST segment 212, and the concavity or elevation of ST segment 212 can also be used to generate characteristic information unique to each user's heartbeat.

T wave 220 can represent the repolarization or recovery of the ventricles. The interval from the beginning of the QRS complex to the apex of the T wave can be referred to as the absolute refractory period. The last half of the T wave can be referred to as the relative refractory period or vulnerable period. The amplitude of T wave 220, the duration of the absolute refractory period, and the relative refractory period can also be used to define a characteristic of the user's heart rate.

QT interval 222, which can represent the total time needed for the ventricles to depolarize and repolarize, can be measured from the beginning of QRS complex 210 to the end of T wave 220. QT interval 222 can typically last between 300 and 450 ms, and can vary based on the condition of the user's heart rate. Several correction factors have been developed to correct QT interval 222 for the heart rate. Both the measured and corrected QT interval 222 values can be used to define a unique characteristic of a user's heartbeat.

Because a user's heartbeat or heart rate can vary slightly based on the user's activity or mood, each authorized user can initially provide a base or standard heart rate, heartbeat, or electrical activity to the device prior to first use. For example, the electronic device can sample several heartbeats or electrical activity at several different times to detect variations in the user's cardiac electrical activity. The electronic device can process detected signals to determine several unique characteristics of the user's heart activity, and identify a range of suitable characteristic values for each of the processed characteristics. Based on the characteristic values and associated ranges, the electronic device can select one, all or a subset of the characteristics to define a unique heart activity profile for the authorized user. The particular combination of characteristics and associated ranges can be selected to minimize overlap with other authorized users, or based on characteristic values and ranges that do not fall within a range of average values and ranges (e.g., do not use characteristic values and ranges that an average user of the device would have).

Figure 3:
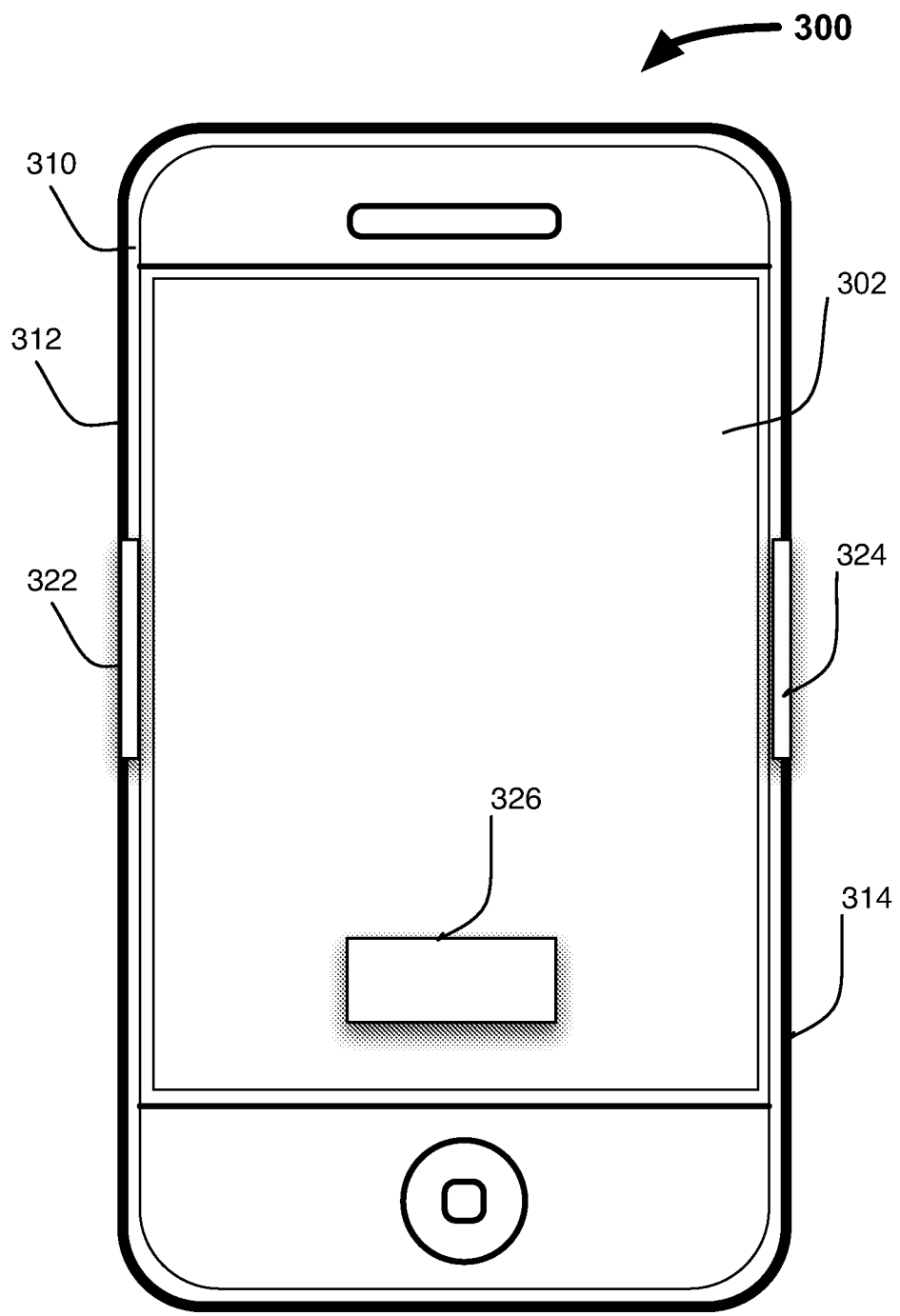
FIG. 3 is a schematic view of an illustrative electronic device having several integrated leads in accordance with one embodiment of the invention.

The heart sensor of the electronic device can include several leads for detecting the user's heart activity. The leads can be integrated in any suitable portion of the electronic device. FIG. 3 is a schematic view of an illustrative electronic device having several integrated leads in accordance with one embodiment of the invention. Electronic device 300 can include display 302 and bezel 310, and be portable such that a user can hold electronic device with fingers extending against one of sides 312 and 314 of bezel 310, and the user's thumb extending against the other of sides 312 and 314. Leads 322 and 324, which can include conductive pads, can be coupled to sides 312 and 314 of bezel 310, respectively, such that when the user holds the device, the user's thumb and fingers are placed in contact with leads 322 and 324. Alternatively, bezel 310 can include any other suitable number of leads, or any other suitable distribution of leads along bezel 310 and in other portions of electronic device 300. The leads can detect the user's cardiac activity through the contact with the user's thumb and fingers, and provide the detected activity to the electronic device processor for processing. The size of leads 322 and 324 can be selected based on any suitable consideration, including for example the different possible positions of a user's hands on the device, the amount of contact necessary to detect the user's cardiac activity, preventing or reducing short circuits and other cardiac signal detection errors, manufacturing considerations (e.g., the minimum or maximum size leads that can be integrated in the bezel), aesthetic considerations (e.g., sizing leads 322 and 324 to reduce the visibility of leads 322 and 324), or any other suitable consideration.

In some embodiments, electronic device 300 can include additional lead 326 embedded in or behind display 302. Lead 326 can be operative to detect a user's heart activity as the user moves a finger across display 302, for example in the vicinity of or directly over lead 326 (e.g., as the user drags a finger over lead 326 to move a slider when unlocking the electronic device). Using lead 326, the electronic device can detect an electrical signal from a different portion of the user's body (e.g., leads 322 and 324 detect signals through a first hand, and lead 326 detects signals through the second hand), which can provide the processor with additional information for determining characteristics of the user's cardiac activity.

Any suitable approach can be used to prevent leads 322, 324 and 326 from shorting. In particular, electronic device 300 can include at least one non-conductive component positioned between each of leads 322, 324 and 326. For example, a rubber gasket can be positioned between leads 322 and 324 (in bezel 310) and lead 326 (in display 302). In some embodiments, the cardiac electrical signals detected by leads 322, 324 and 326 can be faint or have particular characteristics that require materials having particular properties (e.g., silver-based compounds) to detect and transmit. In such cases, although the material used for bezel 310 or other electronic device components can be conductive, its conductivity can be insufficient to transmit signals detected by lead 322 directly to lead 324 (e.g., shorting leads 322 and 324). This may allow leads 322 and 324 to be embedded directly in bezel 310 without the need for additional isolating material, which can add cost and complexity to the manufacturing process.

To ensure that electronic device 300, and in particular bezel 310 remains aesthetically pleasing, leads 322 and 324 can be finished to resemble bezel 310. For example, leads 322 and 324 can be polished or roughened to match the finish of bezel 310. As another example, a conductive coating can be applied to leads 322 and 324 to match the color, tone and reflectivity of bezel 310. In some embodiments, the texture or feel of leads 322 and 324 can also be selected to render leads 322 and 324 visibly and haptically indistinguishable or nearly indistinguishable from bezel 310.

Figure 4A:
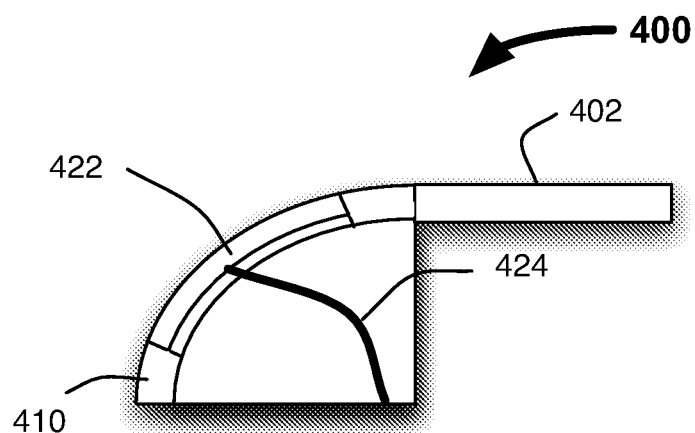
FIG. 4A is a cross-sectional view of an illustrative electronic device having a bezel with an embedded heart sensor lead in accordance with one embodiment of the invention.

Leads 322 and 324 can be integrated in bezel 310 using any suitable approach. In some embodiments, leads 322 and 324 can be positioned on the exterior surface of bezel 310 and include an electrically conductive path to the electronic device processor. FIG. 4A is a cross-sectional view of an illustrative electronic device having a bezel with an embedded heart sensor lead in accordance with one embodiment of the invention. Electronic device 400 can include display 402 and bezel 410. Lead 422 can be embedded along the outer surface of bezel 410 such that lead 422 is exposed to the user during use. Connector 424 can be coupled to the inner surface of lead 422 and extend into electronic device 400 to be coupled with a processor. In some embodiments, electronic device 400 can in addition include an isolating layer positioned between lead 422 and bezel 410 (not shown). The isolating layer can be constructed from any suitable material having non-conductive properties, including for example a ceramic material, plastic, rubber, or any other suitable material. Alternatively, if the material of bezel 410 is not conductive, or insufficiently conductive to cause several distinct leads 422 positioned on bezel 410 from shorting, no isolating layer may be necessary.

Figure 4B:
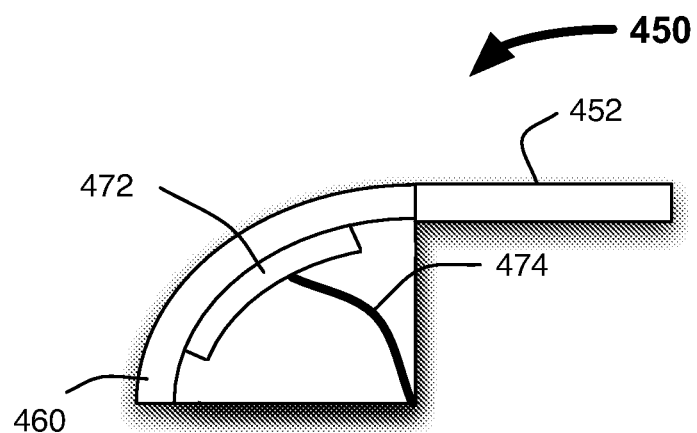
FIG. 4B is a cross-sectional view of another illustrative electronic device having a bezel with an embedded heart sensor lead in accordance with one embodiment of the invention.

FIG. 4B is a cross-sectional view of another illustrative electronic device having a bezel with an embedded heart sensor lead in accordance with one embodiment of the invention. Electronic device 450 can include display 452 and bezel 460. If the electrical conductivity and size of bezel 460, and the strength or characteristics of the cardiac signal provided by the user and detected by the heart sensor are adapted such that the signal can be transmitted along short distances in bezel 460, lead 472 of the heart sensor can be positioned against the back surface of bezel 460. Alternatively, lead 472 can be placed within the thickness of bezel 460 (e.g., in a pocket within the bezel wall), but underneath the outer surface of the bezel. The short thickness of bezel 460 can allow electrical signals to propagate from the user to the outer surface of bezel 460, through bezel 460, and into lead 472, which may in turn transmit the signals to a processor using connector 474. In addition, if several leads are placed along different portions of bezel 460, the distance between adjacent leads can be sufficiently large (e.g., substantially larger than the thickness of bezel 460) that different leads of bezel 460 cannot detect the same electrical signal.

Figure 5:
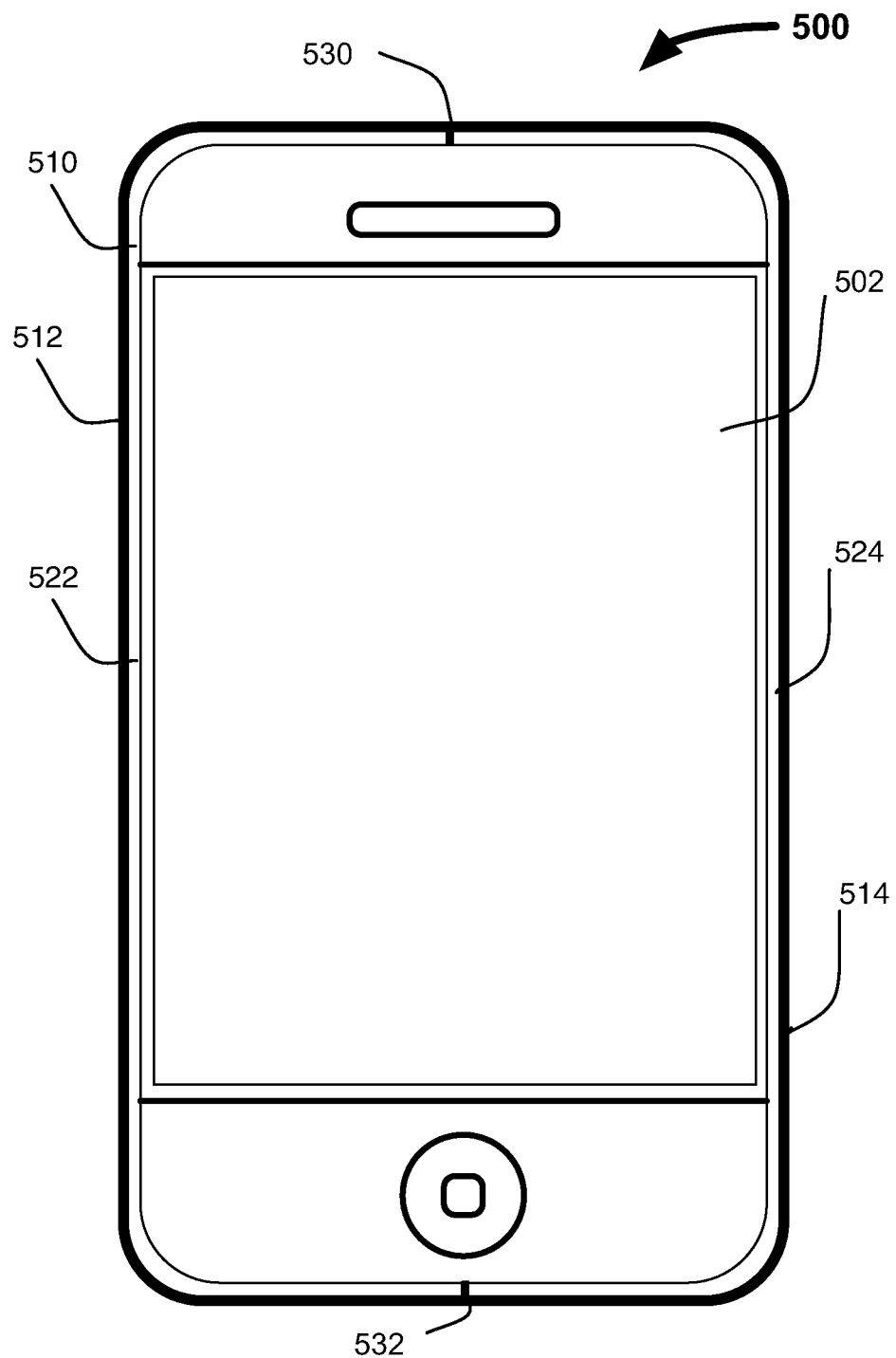
FIG. 5 is a schematic view of an illustrative electronic device using portions of the bezel as leads in accordance with one embodiment of the invention.

In some embodiments, entire portions of the bezel can be used as leads for the heart sensor. FIG. 5 is a schematic view of an illustrative electronic device using portions of the bezel as leads in accordance with one embodiment of the invention. Similar to electronic device 300 (FIG. 3), electronic device 500 can include display 502 and bezel 510. Bezel 510 can be separated into several electrically isolated segments, for example segments 522 and 524. The segments can be electrically isolated using isolating portions 530 and 532, which can be constructed from any suitable non-conductive material, such as for example a composite material, a plastic, rubber, or any other suitable material. Although FIG. 5 shows bezel 510 broken into two segments having similar sizes, it will be understood that bezel 510 can be separated into any suitable number of electrically isolated segments, and each segment can have any suitable size. In particular, the sizes and distribution of each segment can be selected based on physiological considerations (e.g., where a user's hand will be positioned on the device, or aligning the segments to contact particular portions of the user's body).

To ensure that electronic device 500 remains aesthetically pleasing, isolating portions 530 and 532 can be finished to resemble bezel 510. For example, isolating portions 530 and 532 can be polished or machined to create a reflective surface matching the reflection of bezel 510. As another example, a reflective or finishing coating can be applied to the surfaces of isolating portions 530 and 532 to match the finish of bezel 510. In some embodiments, the texture of isolating portions 530 and 532 can also be selected to render segments 522 and 524 visually and haptically indistinguishable or nearly indistinguishable from isolating portions 530 and 532.

Other heart sensor leads can be placed at any other suitable position on the electronic device enclosure. For example, if the enclosure is constructed from a bezel supporting a display and a housing forming the exterior surface of the device behind the display, one or more leads can be embedded in or adjacent to the housing. For example, if the housing includes a conductive section (e.g., a plastic housing with a metallic logo in the center of the housing), the lead can be coupled to or integrated in the conductive section.

The heart sensor and processor can detect and process the user's cardiac activity at any suitable time. For example, the processor can receive and process heart activity when the device is locked and held while in its locked state. As another example, the processor can receive and process heart activity as the user places a finger over lead 326 (e.g., when the user slides a finger across the display to unlock the device) or when an input mechanism detects a particular input. As still another example, the electronic device can receive and process heart activity data in response to a user instruction or request to access a particular application or data that for which access is restricted. Upon receiving the cardiac activity, the electronic device can extract one or more characteristics of the received activity and compare the extracted characteristics with the characteristics previously stored in memory that were associated with authorized users. If the extracted characteristics match those of an authorized user, the electronic device can authenticate the identified user.

The electronic device can perform any suitable operation in response to identifying and authenticating a user based on detected cardiac signals. In some embodiments, the electronic device can provide access to restricted applications, for example applications for which only particular users have licenses or that only particular users have purchased. In some embodiments, the electronic device can provide access to particular data or application settings associated with an authorized user. For example, the electronic device can provide access to the identified user's contact list, or to the identified user's e-mail account or telephone history. As another example, the electronic device can allow the user to access private banking applications, or conduct financial transactions (e.g., transferring funds to different accounts, or purchasing merchandise) using the electronic device. In some embodiments, the electronic device can load user settings and profiles for providing a customized display to the user. For example, the electronic device can display icons or options in the manner set by the user, or provide displays using a color scheme, fonts, or other customizable display attribute that are associated with the identified user.

In some embodiments, the electronic device can use the detected heart rate or heartbeat characteristics to determine the user's mood. In particular, because the allowable determined characteristics associated with each user can include a range of values, the electronic device can determine the distribution of the detected characteristics in the allowable characteristic ranges. Using the determined distribution, the electronic device can establish a user's mood and provide electronic device operations or data (e.g., media) associated with the extrapolated mood. Systems and methods for providing mood-based electronic device operations are discussed in more detail in commonly assigned U.S. Patent Application Publication No. 2010/0011388, published Jan.

14, 2010, and entitled "System and Method for Creating Playlists Based on Mood," which is incorporated by reference herein in its entirety.

In some embodiments, the electronic device can provide media playback based on the user's detected cardiac signal. For example, the electronic device can identify media having beats per minute or other characteristics that are associated with or related to the user's cardiac signal or heart rate, and play back the identified media. As another example, the media provided can have beats per minute faster or slower than the user's current heart rate to direct the user to work harder (e.g., during a workout) or to cool or calm the user down (e.g., at the end of a workout).

Figure 6:
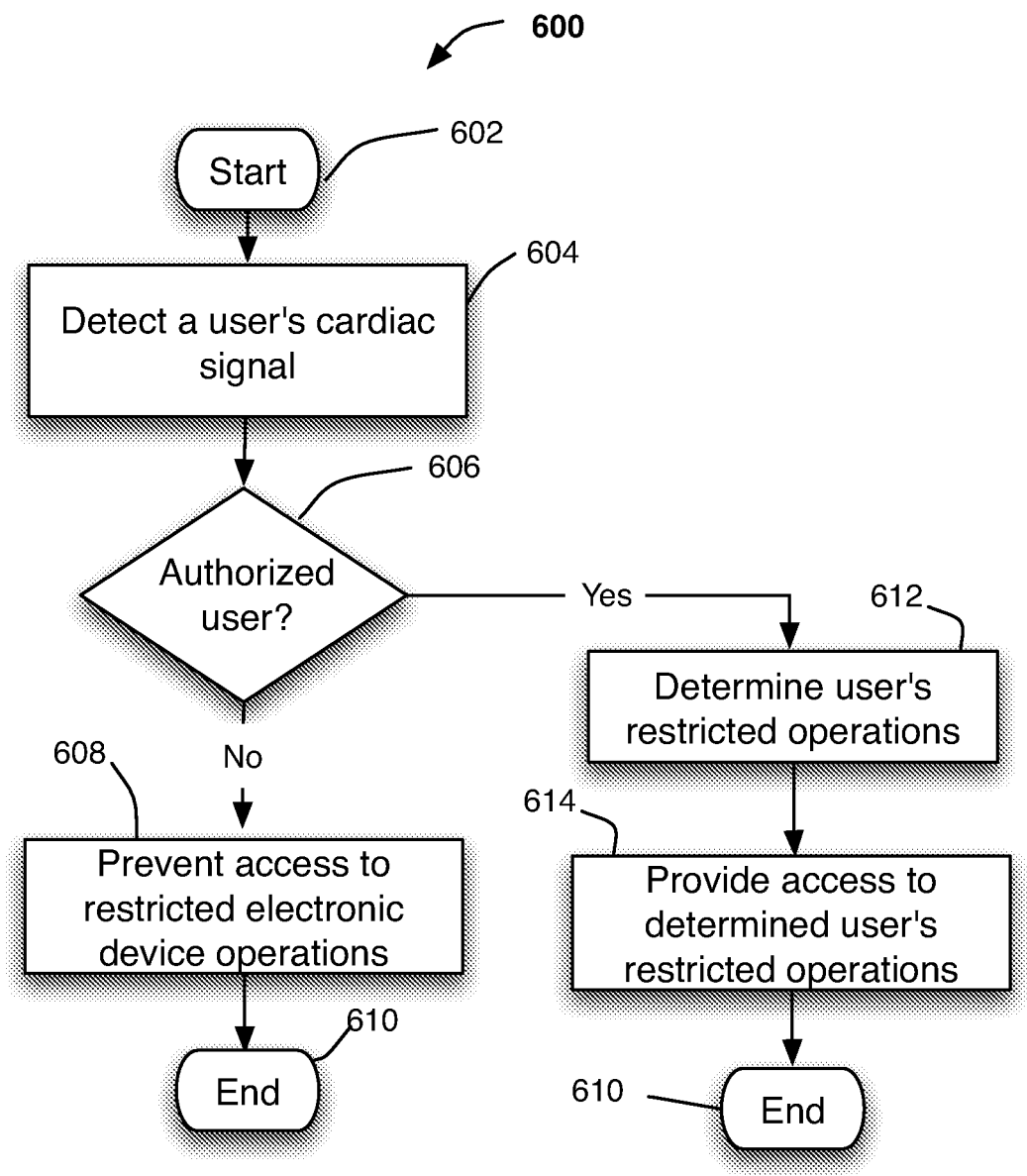
FIG. 6 is a flowchart of an illustrative process for performing an electronic device operation based on a user's cardiac signal in accordance with one embodiment of the invention.

FIG. 6 is a flowchart of an illustrative process for performing an electronic device operation based on a user's cardiac signal in accordance with one embodiment of the invention. Process 600 can begin at step 602. At step 604, the electronic device can detect a user's cardiac signal. For example, the electronic device can detect a user's heart rate or heart beat using one or more leads connected to or placed on a housing, bezel, or other exterior surface of the electronic device. The electronic device can process the received signal using any suitable approach, including for example to determine unique characteristics of the signal. Such characteristics can include, for example, durations between peaks in an EKG signal, peak values or rations between peaks in the EKG signal, or any other suitable characteristic. At step 606, the electronic device can determine whether the user detected at step 604 is an authorized user. For example, the electronic device can compare the determined characteristics of the detected cardiac signals with a library of signals associate with known authorized users. If the electronic device determines that the user is not authorized (e.g., the characteristics of the detected cardiac signal do not match characteristics of a cardiac signal stored in memory), process 600 can move to step 608.

At step 608, the electronic device can prevent access to restricted electronic device operations. For example, the electronic device can prevent the user from accessing personal or private information associated with other users. As another example, the electronic device can prevent the user from accessing applications or operations associated with particular users (e.g., applications purchased by particular users). As still another example, the electronic device can prevent the user from accessing any electronic device operation (e.g., no operation except for emergency calls). Process 600 can then end at step 610.

If, at step 606, the electronic device instead determines that the user is authorized, process 600 can move to step 612. At step 612, the electronic device can determine the restricted operations that are associated with the user. For example, the electronic device can determine the particular private data associated with the authorized user (e.g., e-mail accounts, contact lists and banking information). As another example, the electronic device can determine the particular operations or applications associated with the authorized user (e.g., applications purchased by the user using an applications store, or system controlling operations associated with an administrative account). At step 614, the electronic device can provide access to the user's determined restricted operations. For example, the electronic device can load determined data. As another example, the electronic device can provide links for launching determined personal or private applications. Process 600 can then end at step 610.

The above-described embodiments of the present invention are presented for purposes of illustration and not of limitation, and the present invention is limited only by the claims which follow.

What is claimed is:

1. An electronic device operative to detect a user's cardiac signal, comprising:
   a housing;
   a bezel that comprises a first portion and a second portion and that is coupled to the housing to form at least a portion of an enclosure for the electronic device;
   a heart sensor operative to detect the user's cardiac signal, the heart sensor comprising:
      a first lead embedded in the first portion, wherein the first lead is configured to detect a first electrical signal of the user's cardiac signal via the user's contact with at least one of the first lead and the first portion; and
      a second lead embedded in the second portion, wherein the second lead is configured to detect a second electrical signal of the user's cardiac signal via the user's contact with at least one of the second lead and the second portion; and
   a processor coupled to the heart sensor and operative to receive and process the detected cardiac signal.

2. The electronic device of claim 1, wherein:
   the first portion and the second portion are located on opposite sides of the electronic device.

3. The electronic device of claim 2, wherein the first portion is electrically isolated from the second portion.

4. The electronic device of claim 1, wherein the bezel further comprises a third portion, and wherein:
   the first portion is separated from the second portion by the third portion;
   at least the third portion of the bezel is constructed from a material having a first conductivity; and
   the first conductivity is insufficient to transmit the first electrical signal from the first lead to the second lead via the third portion.

5. The electronic device of claim 4, wherein the material having the first conductivity comprises one of aluminum and steel, and wherein the second lead is constructed from a silver based compound.

6. The electronic device of claim 1, wherein:
   the second lead is configured to detect the second electrical signal of the user's cardiac signal via the user's contact with an exterior surface of the second portion;
   the second lead is positioned from the exterior surface of the second portion by a thickness of the second portion of the bezel;
   at least the thickness of the second portion of the bezel is constructed from a material having a second conductivity; and
   the second conductivity is defined such that the second electrical signal is not transmitted over a distance substantially larger than the thickness of the second portion of the bezel.

7. The electronic device of claim 6, wherein the first lead and the second lead are positioned apart from one another at a distance substantially larger than the thickness of the second portion of the bezel.

8. The electronic device of claim 1, wherein:
   the bezel further comprises at least one pocket underneath an outer surface of the bezel; and
   at least one of the first lead and the second lead is placed within the at least one pocket.

9. The electronic device of claim 1, wherein an exterior surface of the bezel comprises an exterior surface of the first portion, and wherein the first lead is positioned underneath the exterior surface of the first portion.

10. The electronic device of claim 9, wherein the first lead is configured to detect the first electrical signal via the user's contact with the exterior surface of the first portion.

11. The electronic device of claim 1, wherein the processor is positioned within the enclosure.

12. The electronic device of claim 1, further comprising a third lead embedded in the housing, wherein the third lead is configured to detect a third electrical signal of the user's cardiac signal via the user's contact with at least one of the third lead and the housing.

13. The electronic device of claim 1, further comprising:
 a display, wherein the bezel supports the display, and wherein the housing forms an exterior surface of the electronic device behind the display; and
 a third lead embedded with the display, wherein the third lead is configured to detect a third electrical signal of the user's cardiac signal via the user's contact with at least one of the third lead and the display.

14. A bezel for use in an electronic device operative to detect a user's cardiac signal, the bezel operative to be coupled to a housing to form an electronic device enclosure, the bezel comprising:
 a first portion;
 a second portion;
 a first heart sensor lead positioned within the first portion of the bezel, wherein the user's contact with at least one of the first heart sensor lead and the first portion of the bezel provides a first electrical signal of the user's cardiac signal to the first heart sensor lead; and
 a second heart sensor lead positioned within the second portion of the bezel, wherein the user's contact with at least one of the second heart sensor lead and the second portion of the bezel provides a second electrical signal of the user's cardiac signal to the second heart sensor lead.

15. The bezel of claim 14, wherein the bezel is constructed from a conductive material.

16. The bezel of claim 15 further comprising a third portion, wherein:
 the first portion is separated from the second portion by the third portion; and
 a conductivity of the third portion of the bezel is defined to prevent a transmission of the first electrical signal from the first portion to the second portion via the third portion.

17. The bezel of claim 14, wherein:
 at least one of the first portion and the second portion comprises a first finish; and
 at least one of the first heart sensor lead and the second heart sensor lead comprises a second finish that matches the first finish.

18. The bezel of claim 14, further comprising an isolating layer placed between the first portion of the bezel and the first heart sensor lead, wherein the isolating layer prevents the first electrical signal from being transmitted to the first portion.

19. The bezel of claim 14, wherein the bezel is constructed from one of steel and aluminum.

20. The bezel of claim 14, wherein at least one of the first pad and the second pad is constructed from a silver based compound.

* * * * *